United States Patent
Mori et al.

[11] Patent Number: 6,005,119
[45] Date of Patent: Dec. 21, 1999

[54] PROCESS FOR PREPARING PYRROLIDINE DERIVATIVES

[75] Inventors: Natsuki Mori, Kakogawa; Noritaka Yoshida, Matsubara; Takeshi Furuta, Takasago; Kazunori Kan, Nishinomiya, all of Japan

[73] Assignee: Kaneka Corporation, Osaka, Japan

[21] Appl. No.: 09/171,996

[22] PCT Filed: Apr. 22, 1997

[86] PCT No.: PCT/JP97/01373

§ 371 Date: Apr. 5, 1999

§ 102(e) Date: Apr. 5, 1999

[87] PCT Pub. No.: WO97/40008

PCT Pub. Date: Oct. 30, 1997

[30] Foreign Application Priority Data

Apr. 22, 1996 [JP] Japan ................................. 8-126361
Jan. 9, 1997 [JP] Japan ................................. 9-014639

[51] Int. Cl.⁶ .................................................. C07D 207/12
[52] U.S. Cl. ........................................... 548/556; 548/566
[58] Field of Search ................................... 548/556, 566

[56] References Cited

U.S. PATENT DOCUMENTS

| | | | |
|---|---|---|---|
| 4,810,703 | 3/1989 | Shanklin, Jr. et al. | 514/212 |
| 4,851,418 | 7/1989 | Sanchez | 514/300 |
| 5,387,591 | 2/1995 | Lavielle et al. | 514/307 |
| 5,407,946 | 4/1995 | Lavielle et al. | 514/314 |

FOREIGN PATENT DOCUMENTS

| | | | |
|---|---|---|---|
| 0 012 071 A1 | 6/1980 | European Pat. Off. . | |
| 0 556 119 A1 | 8/1993 | European Pat. Off. . | |
| 61-100563 | 5/1986 | Japan | 514/212 |
| 61-169763 | 7/1987 | Japan | 514/212 |
| 63-41453 | 2/1988 | Japan | 514/212 |
| 2-218664 | 8/1990 | Japan | 514/212 |
| 3-176463 | 7/1991 | Japan | 514/212 |
| 5-58995 | 7/1991 | Japan | 514/212 |
| 4-95067 | 3/1992 | Japan | 514/212 |

OTHER PUBLICATIONS

Naylor et al, "4–[(Alkylamino)methyl]furo[3,2–c]pyridines: A New Series of Selective kReceptor Agonists", *Journal of Medicinal Chemistry*, vol. 37, No. 14, 1994, pp. 2138–2144.

*Primary Examiner*—Joseph K. McKane
*Attorney, Agent, or Firm*—Pollock, Vande Sande & Amernick

[57] ABSTRACT

It is an object of the present invention to provide a process for producing an pyrrolidine derivative of general formula (2) or a salt thereof in a simple and economical manner and with good productivity and high yields.

The present invention consists in a process for producing a pyrrolidine derivative of the general formula (2) or a salt thereof which comprises subjecting a compound of the general formula (1) to hydrogenolysis using a metal catalyst in the presence of at least one protic acid selected from the group consisting of hydrochloric acid, sulfuric acid, phosphoric acid, p-toluenesulfonic acid, methanesulfonic acid, acetic acid, n-butyric acid, trifluoroacetic acid and oxalic acid.

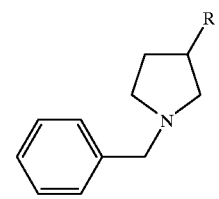

(1)

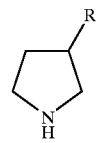

(2)

R represents a 1-cyano-1,1-diphenylmethyl, 1-carbamoyl-1,1-diphenylmethyl, n-butyryloxy, methanesulfonyloxy or p-toluenesulfonyloxy group.

11 Claims, No Drawings

PROCESS FOR PREPARING PYRROLIDINE DERIVATIVES

TECHNICAL FIELD

The present invention relates to a process for producing a pyrrolidine derivative of the general formula (2):

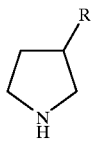

(2)

(wherein R represents a 1-cyano-1,1-diphenylmethyl, 1-carbamoyl-1,1-diphenylmethyl, n-butyryloxy, methanesulfonyloxy or p-toluenesulfonyloxy group) or a salt thereof, which is useful as an intermediate for the synthesis of medicinals, agrochemicals and other chemicals.

BACKGROUND ART

As a process for producing the above-mentioned pyrrolidine derivative of general formula (2) or a salt thereof using compounds of the general formula (1):

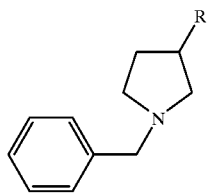

(1)

(wherein R is as defined above) as a starting material, a process is known (Japanese Kokai Publication Sho-61-100563) which comprises once synthesizing methyl 3-(1-cyano-1,1-diphenylmethyl)-1-pyrrolidinecarboxylate starting with 1-benzyl-3-(1-cyano-1,1-diphenylmethyl)-pyrrolidine and then converting the former to 3-(1-cyano-1,1-diphenylmethyl)-pyrrolidine. However, this process involves long steps and complicated operation and gives low yields, hence can hardly be said to be an industrial production process.

Another process is also known (Japanese Kokoku Publication Hei-07-72171) for producing 3-(1-carbamoyl-1,1-diphenylmethyl)-pyrrolidine by subjecting 1-benzyl-3-(1-carbamoyl-1,1-diphenylmethyl)-pyrrolidine to hydrogenolysis using palladium-carbon. However, it uses a large amount of palladium, which is expensive, and requires a long reaction time. Thus, it has problems as an industrial production process from the viewpoints of economy and productivity.

Furthermore, no process is known for producing 3-methanesulfonyloxypyrrolidine or a salt thereof by debenzylating 1-benzyl-3-methanesulfonyloxypyrrolidine, for producing 3-p-toluenesulfonyloxypyrrolidine or a salt thereof by debenzylating 1-benzyl-3-p-toluenesulfonyloxypyrrolidine, or for producing 3-n-butyryloxypyrrolidine or a salt thereof by debenzylating 1-benzyl-3-n-butyryloxypyrrolidine.

Accordingly, the development of a process for producing the above-mentioned pyrrolidine derivative of general formula (2) or a salt thereof in a simple and economical manner and with good productivity and high yields by debenzylating the above-mentioned compound of general formula (1) has been desired.

SUMMARY OF INVENTION

In view of the foregoing, it is an object of the present invention to provide a process for producing the above-mentioned pyrrolidine derivative of general formula (2) or a salt thereof in a simple and economical manner and with good productivity and high yields.

The present invention consists in a process for producing a pyrrolidine derivative of the general formula (2):

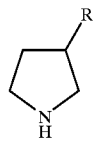

(2)

(wherein R is as defined above) or a salt thereof which comprises subjecting a compound of the general formula (1):

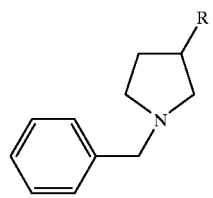

(1)

(wherein R is as defined above) to hydrogenolysis using a metal catalyst in the presence of at least one protic acid selected from the group consisting of hydrochloric acid, sulfuric acid, phosphoric acid, p-toluenesulfonic acid, methanesulfonic acid, acetic acid, n-butyric acid, trifluoroacetic acid and oxalic acid.

DETAILED DISCRIPTION OF THE INVENTION

The present invention is described in detail in the following.

The above-mentioned compound of general formula (1) which is to be used in the process of the present invention can be produced by the processes described, for example, in Japanese Kokai Publications Sho-61-100563, Hei-01-113365, Hei-01-141600 and Hei-01-143852.

The protic acid to be used in accordance with the present invention is at least one species selected from the group consisting of hydrochloric acid, sulfuric acid, phosphoric acid, p-toluenesulfonic acid, methanesulfonic acid, acetic acid, n-butyric acid, trifluoroacetic acid and oxalic acid. Among them, hydrochloric acid, sulfuric acid and oxalic acid are preferred.

It is sufficient that said protic acid be used in an amount of about 1 equivalent relative to the above-mentioned compound of general formula (1), which is the starting material.

In the practice of the present invention, said protic acid may be charged together with the above-mentioned starting compound of general formula (1), a reaction solvent and a metal catalyst. Alternatively, a salt of the above-mentioned compound of general formula (1) with said protic acid may be prepared beforehand and the salt may be charged together with the reaction solvent and metal catalyst.

As the metal catalyst to be used in the process of the present invention, there may be mentioned, for example, ruthenium, rhodium, platinum, palladium and the like. These may be used either singly or in combination of two or more. These may be used as metal catalysts themselves or in the form supported on active carbon. The use of palladium-carbon is preferred, however.

Said metal catalyst is used preferably in an amount of 0.001 to 20% by weight, more preferably 0.1 to 5% by weight, relative to the above-mentioned compound of general formula (1).

As the reaction solvent mentioned above, there may be mentioned, for example, alcohols such as methanol, ethanol, n-propanol, isopropanol and the like; hydrocarbons such as benzene, toluene, cyclohexane and the like; ethers such as diethyl ether, tetrahydrofuran, dioxane and the like; esters such as ethyl acetate, butyl acetate and the like; methylene chloride, dimethylformamide and other organic solvents; and water. These may be used alone or two or more of them may be used in admixture. Among them, the use of an alcohol or a mixed solvent composed of an alcohol and water is preferred.

Said reaction solvent is preferably used in an amount of 0.1 to 10 times, more preferably 0.3 to 3 times, still more preferably 0.3 to 1.5 times as much as the amount of the above-mentioned compound of general formula (1).

The reaction temperature for the above reaction is preferably 0 to 100° C. more preferably 20 to 70° C. still more preferably 50 to 60° C.

In the above reaction, the hydrogen pressure may be selected arbitrarily according to the equipment available. The range from an atmospheric pressure to 300 kPa is preferred, however.

In the process of the present invention, when the above-mentioned compound of general formula (1) is optically active, the above-mentioned pyrrolidine derivative of general formula (2) or a salt thereof can be obtained in the corresponding optically active form, without racemization.

As the optically active form of the above-mentioned pyrrolidine derivative of general formula (2) or a salt thereof, there may be mentioned, for example, (S)-3-(1-cyano-1,1-diphenylmethyl)-pyrrolidine, (R)-3-(1-cyano-1,1-diphenylmethyl)-pyrrolidine, (S)-3-(1-carbamoyl-1,1-diphenylmethyl)-pyrrolidine, (R)-3-(1-carbamoyl-1,1-diphenylmethyl)-pyrrolidine, (S)-3-methanesulfonyloxypyrrolidine, (R)-3-methanesulfonyloxypyrrolidine, (S)-3-p-toluenesulfonyloxypyrrolidine, (R)-3-p-toluenesulfonyloxypyrrolidine, (S)-3-n-butyryloxypyrrolidine, (R)-3-n-butyryloxypyrrolidine and the like.

In accordance with the present invention, the above-mentioned compound of general formula (1) is subjected to hydrogenolysis using the above-mentioned metal catalyst in the presence of the above-mentioned protic acid, whereby the above-mentioned pyrrolidine derivative of general formula (2) or a salt thereof can be obtained.

As the salt of the above-mentioned pyrrolidine derivative, there may be mentioned, for example, the salt with the protic acid used for the reaction, and salts with other acids.

In the present invention, the synthesized pyrrolidine derivative of general formula (2) mentioned above or a salt thereof can be isolated and purified in the free form or in the form of a salt with the protic acid by separating the metal catalyst from the reaction mixture by filtration, centrifugation or the like, followed by a conventional treatment method such as concentration, solvent extraction, distillation, crystallization and/or the like.

BEST MODES FOR CARRYING OUT THE INVENTION

The following examples illustrate the present invention in further detail. However, said examples are by no means limitative of the scope of the present invention.

EXAMPLE 1

A mixed solution obtained by mixing 3.9 g of 79% pure (S)-1-benzyl-3-(1-cyano-1,1-diphenylmethyl)-pyrrolidine with 3.1 ml of ethanol and adding dropwise 446 mg of 97% sulfuric acid thereto with cooling on an ice-water bath was charged, together with 158 mg of moist 5% palladium-carbon (water content 52% by weight), into an autoclave, hydrogen was introduced thereinto and the autoclave was heated to raise the temperature to 60 and the pressure to 203 kPa, and the reaction was allowed to proceed for 3.5 hours. After completion of the reaction, the reaction mixture was cooled to room temperature and depressurized. The reaction mixture was taken out, the catalyst was filtered off, the filtrate obtained was concentrated under reduced pressure, toluene and water were added to the thus-obtained oily concentrate, and the pH was adjusted to 13 by adding dropwise 30% aqueous sodium hydroxide with stirring on an ice-water bath. The toluene layer was recovered, the aqueous layer was further extracted with toluene, and the toluene layers were combined, washed with a saturated aqueous solution of sodium chloride, dried with anhydrous sodium sulfate and, after filtration, concentrated under reduced pressure, to give an oil. This was purified by silica gel column chromatography using, as an eluant, dichloromethane containing methanol (0% to 10%). Main fractions containing the product were combined and concentrated under vacuum to give (S)-3-(1-cyano-1,1-diphenylmethyl)-pyrrolidine in a yield of 84 mole percent.

EXAMPLE 2

The procedure of Example 1 was followed except that the autoclave was charged with 3.9 g of 79% pure (S)-1-benzyl-3-(1-cyano-1,1-diphenylmethyl)-pyrrolidine, 3.1 ml of ethanol, 786 mg of oxalic acid and 158 mg of moist 5% palladium-carbon (water content 52% by weight) and that hydrogen was introduced thereinto and the autoclave was heated to thereby raise the temperature to 60° C. and the pressure to 203 kPa and the reaction was allowed to proceed for 3.5 hours. (S)-3-(1-Cyano-1,1-diphenylmethyl)-pyrrolidine was obtained in a yield of 70 mole percent.

EXAMPLE 3

A mixed solution obtained by mixing 3.5 g of 79% pure (S)-1-benzyl-3-(1-cyano-1,1-diphenylmethyl)-pyrrolidine with 2.8 ml of ethanol and adding dropwise 0.72 ml of 35% aqueous hydrochloric acid thereto with cooling on an ice-water bath was charged, together with 139 mg of moist 5% palladium-carbon (water content 52% by weight), into an autoclave, hydrogen was introduced thereinto and the autoclave was heated to raise the temperature to 60° C. and the pressure to 203 kPa, and the reaction was allowed to proceed for 3 hours. Hydrogen absorption came to an end in 2.6 hours after the start of hydrogen introduction. After completion of the reaction, the reaction mixture was cooled to room temperature and depressurized. The reaction mixture was taken out, the catalyst was filtered off, the filtrate obtained was concentrated under reduced pressure, toluene and water were added to the thus-obtained oily concentrate, and the pH was adjusted to 13 by adding dropwise 30% aqueous sodium hydroxide with stirring on an ice-water bath. The toluene layer was recovered, the aqueous layer was further extracted with toluene, and the toluene layers were combined, washed with a saturated aqueous solution of sodium chloride, dried with anhydrous sodium sulfate and, after filtration, concentrated under reduced pressure and further dried under vacuum to give 2.1 g of (S)-3-(1-cyano-1,1-diphenylmethyl)-pyrrolidine as an oil (yield: 91 mole percent).

Toluene content: 7.5% $[\alpha]_D^{25}$+13.1° (c=1.0, $CH_2Cl_2$)

EXAMPLE 4

A mixed solution obtained by mixing 2.3 g of 100% pure (S)-1-benzyl-3-methanesulfonyloxypyrrolidine with 3.0 ml of ethanol and adding dropwise 1.00 ml of 35% aqueous hydrochloric acid thereto with cooling on an ice-water bath was charged, together with 300 mg of moist 5% palladium-carbon (water content 52% by weight), into an autoclave, hydrogen was introduced thereinto and the autoclave was heated to raise the temperature to 60 and the pressure to 203 kPa, and the reaction was allowed to proceed for 4 hours. Hydrogen absorption came to an end in 3.2 hours after the start of hydrogen introduction. After completion of the reaction, the reaction mixture was cooled to room temperature and depressurized. The reaction mixture was taken out, the catalyst was filtered off, and the filtrate obtained was concentrated under reduced pressure and further dried under vacuum to give 2.4 g (yield: 84 mole percent) of (S)-3-methanesulfonyloxypyrrolidine hydrochloride.

EXAMPLE 5

A mixed solution obtained by mixing 3.0 g of 100% pure (R)-1-benzyl-3-p-toluenesulfonyloxypyrrolidine with 3.0 ml of ethanol and adding dropwise 0.80 ml of 35% aqueous hydrochloric acid thereto with cooling on an ice-water bath was charged, together with 150 mg of moist 5% palladium-carbon (water content 52% by weight), into an autoclave, hydrogen was introduced thereinto and the autoclave was heated to raise the temperature to 60 and the pressure to 203 kPa, and the reaction was allowed to proceed for 4.5 hours. Hydrogen absorption came to an end in 2.5 hours after the start of hydrogen introduction. After completion of the reaction, the reaction mixture was treated in the same manner as in Example 4 to give 2.51 g (yield: 86 mole percent) of (R)-3-p-toluenesulfonyloxypyrrolidine hydrochloride.

EXAMPLE 6

A mixed solution obtained by mixing 3.0 g of 100% pure (R,S)-1-benzyl-3-n-butyryloxypyrrolidine with 3.0 ml of ethanol and adding dropwise 1.06 ml of 35% aqueous hydrochloric acid thereto with cooling on an ice-water bath was charged, together with 450 mg of moist 5% palladium-carbon (water content 52% by weight), into an autoclave, hydrogen was introduced thereinto and the autoclave was heated to raise the temperature to 60 and the pressure to 203 kPa, and the reaction was allowed to proceed for 4 hours. Hydrogen absorption came to an end in 3 hours after the start of hydrogen introduction. After completion of the reaction, the reaction mixture was treated in the same manner as in Example 4 to give 2.35 g (yield: 92 mole percent) of (R,S)-3-n-butyryloxypyrrolidine hydrochloride.

$^1$N-NMR ($CDCl_3$): δ=5.4 (brs, 1H), 3.7 to 3.4 (m, 4H), 2.4 to 2.2. (m, 4H), 1.7 to 1.6 (m, 2H), 0.9 (t, 3H).

To 2.0 g of the thus-obtained (R,S)-3-n-butyryloxypyrrolidine hydrochloride was added dichloromethane, and the mixture was made basic by adding dropwise thereto a saturated aqueous solution of sodium bicarbonate with cooling on an ice-water bath. The dichloromethane layer was recovered, the aqueous layer was further extracted with dichloromethane, and the dichloromethane layers were combined, washed with a saturated aqueous solution of sodium chloride, dried over anhydrous sodium sulfate and, after filtration, concentrated under reduced pressure to give 1.2 g of (R,S)-3-n-butyryloxypyrrolidine.

$^1$N-NMR ($CDCL_3$): δ=5.2 (brs, 2H), 3.2 to 2,9 (m, 4H), 2.4 to 2.2 (m, 2H), 2.1 to 2.0 (m, 1H), 1.9 to 1.8 (m, 1H), 1.7 to 1.6 (m, 2H), 0.9 (t, 3H).

COMPARATIVE EXAMPLE 1

An autoclave was charged with 3.9 g of 79% pure (S)-1-benzyl-3-(1-cyano-1,1-diphenylmethyl)-pyrrolidine, 3 ml of ethanol and 156 mg of moist 5% palladium-carbon (water content 52% by weight), hydrogen was introduced thereinto and the autoclave was heated to raise the temperature to 60 and the pressure to 203 kPa, and the reaction was allowed to proceed. Five hours after the start of hydrogen introduction, no hydrogen absorption was observed any more, so that the reaction mixture was cooled to room temperature and depressurized. The reaction mixture was taken out, the catalyst was filtered off, and the filtrate obtained was analyzed by high performance liquid chromatography. (S)-3-(1-cyano-1,1-diphenylmethyl)-pyrrolidine was obtained in a yield of 36 mole percent.

INDUSTRIAL APPLICABILITY

According to the present invention, an 3-substituted pyrrolidine derivative or a salt thereof, which is useful as an intermediate for the synthesis of medicinals and agrochemicals, can be produced in a simple and economical manner and with good productivity and high yields, as mentioned hereinabove.

We claim:

1. A process for producing a pyrrolidine compound of the general formula (2):

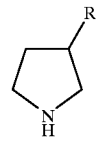

(2)

wherein R represents a 1-cyano-1,1-diphenylmethyl, n-butyryloxy, methanesulfonyloxy, or p-toluenesulfonyloxy group or a salt thereof which comprises subjecting a compound of the general formula (1):

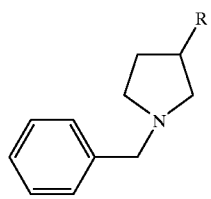

wherein R is as defined above, to hydrogenolysis using a metal catalyst in the presence of at least one protic acid selected from the group consisting of hydrochloric acid, sulfuric acid, phosphoric acid, p-toluenesulfonic acid, methanesulfonic acid, acetic acid, n-butyric acid, trifluoroacetic acid and oxalic acid.

2. A process for producing a pyrrolidine compound or a salt thereof according to claim 1, wherein the compound of general formula (1) is in an optically active form and the pyrrolidine compound of general formula (2) or a salt thereof is in an optically active form.

3. A process for producing a pyrrolidine compound or a salt thereof according to claim 1, wherein the metal catalyst is at least one species selected from the group consisting of ruthenium, rhodium, platinum and palladium.

4. A process for producing a pyrrolidine compound or a salt thereof according to claim 1, wherein the protic acid is hydrochloric acid, sulfuric acid, acetic acid or oxalic acid.

5. A process for producing a pyrrolidine compound or a salt thereof according to claim 1, wherein the amount of the metal catalyst is 0.1 to 5% by weight of the compound of the general formula (1).

6. A process for producing a pyrrolidine compound or a salt thereof according to claim 2, wherein the metal catalyst is at least one species selected from the group consisting of ruthenium, rhodium, platinum and palladium.

7. A process for producing a pyrrolidine compound or a salt thereof according to claim 2, wherein the protic acid is hydrochloric acid, sulfuric acid, acetic acid or oxalic acid.

8. A process for producing a pyrrolidine compound or a salt thereof according to claim 3 wherein the protic acid is hydrochloric acid, sulfuric acid, acetic acid or oxalic acid.

9. A process for producing a pyrrolidine compound or a salt thereof according to claim 2, wherein the amount of the metal catalyst is 0.1 to 5% by weight of the compound of the general formula (1).

10. A process for producing a pyrrolidine compound or a salt thereof according to claim 3, wherein the amount of the metal catalyst is 0.1 to 5% by weight of the compound of the general formula (1).

11. A process for producing a pyrrolidine compound or a salt thereof according to claim 4, wherein the amount of the metal catalyst is 0.1 to 5% by weight of the compound of the general formula (1).

\* \* \* \* \*